United States Patent
Semba

(10) Patent No.: US 6,387,659 B1
(45) Date of Patent: May 14, 2002

(54) PROCESS FOR PRODUCING S-HYDROXYNITRILE LYASE

(75) Inventor: Hisashi Semba, Ibaraki (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/472,146

(22) Filed: Dec. 27, 1999

(30) Foreign Application Priority Data

Dec. 28, 1998 (JP) ........................................... 10-373246
Dec. 28, 1998 (JP) ........................................... 10-373247
Dec. 28, 1998 (JP) ........................................... 10-373248

(51) Int. Cl.$^7$ ..................... C12P 21/00; C12N 15/63; C07H 21/04
(52) U.S. Cl. .................. 435/69.1; 435/320.1; 536/23.1; 536/24.1
(58) Field of Search ............................. 435/6, 18, 69.1, 435/320.1, 471; 530/370; 536/23.1

(56) References Cited

U.S. PATENT DOCUMENTS 5,885,809 A    3/1999   Effenberger et al. ........ 435/128

FOREIGN PATENT DOCUMENTS

EP     0 969 095 A2    1/2000
WO     WO 97/03204    1/1997

OTHER PUBLICATIONS

Forster et al. The first recombinant hydroxynitrile lyase and its application in the synthesis of (S)–cyanohydrins Angew. Chem. Int. Ed. Engl. vol. 35(4):437–439, Apr. 1996.*

Hughes et al. Production and characterization of a plant alpha–hydroxynitrile lyase in *Escherichia coli*. Biotechnol. and Bioengineering. vol. 53(3): 332–338, Mar. 1997.*

Hasslacher et al. Molecular cloning of the full–length cDNA of (S)–hydroxynitrile lyase from *Hevea brasiliensis*. J. Biol. Chem. vol. 271(10):5884–5891, Mar. 1996.*

Hasslacher et al. High–level intracellular expression of hydroxynitrile lyase from the tropical rubber tree *Hevea brasiliensis* in microbial hosts. Prot. Expression and Purification. vol. 11:61–71. ('97A), Jul. 1997.*

Hasslacher et al. Hydroxynitrile lyase from *Hevea brasiliensis*: Molecular characterization and mechanism of enzyme catalysis. Proteins: Structure, Function and Genetics. vol. 27:438–449, Mar. 1997.*

Klaus Trummler et al., "Expression of the $Zn^{2+}$–containing hydroxynitrile lyase from flax (*Linum usitatissimum*) in *Pichia pastoris*—utilization of the recombinant enzyme for enzymatic analysis and site–directed mutagenesis," *Plant Science*, vol. 139, pp. 19–27, 1998.

Harald Wajant and Klaus Pfizenmaier, "Identification of Potential Active–site Residues in the Hydroxynitrile Lyase from *Manihot esculenta* by Site–directed Mutagenesis," *The Journal of Biological Chemistry*, vol. 271, No. 42, pp. 25830–25834, 1996.

EPO Search Report dated 2001.

Abstract 2000125886, Jun. 5, 2001.

M. Hasslacher et al., "Molecular Cloning of the Full–length cDNA of (S)–Hydroxynitrile Lyase from *Hevia brasiliensis*," *The Journal of Biological Chemistry*, vol. 271, No. 10, pp. 5884–5891 (1996).

J. Hughes, et al., Purification, Characterization, and Cloning of α–Hydroxynitrile Lyase from Cassava (*Manihot esculenta* Crantz), *Archives of Biochemistry and Biophysics*, vol. 311, No. 2, pp. 496–502, (1994).

J. Hughes, et al., Production and Characterization of a Plant α–Hydroxynitrile Lyase in *Escherichia coli*, *Biotechnology and Bioengineering*, vol. 53, No. 3, pp. 332–338, (1997).

M. Hasslacher et al., "High–Level Intracellular Expression of Hydroxynitrile Lyase from the Tropical Rubber Tree *Hevea brasiliensis* in Microbial Hosts," *Protein Expression and Purification*, vol. 11, pp. 61–71 (1997).

S. Förster, et al., "The First Recombinant Hydroxynitrile Lyase and its Application in the Synthesis of (S)–Cyanohydrins," *Angew. Chem. Int. Ed. Engl.*, vol. 35, No. 4, pp. 437–439 (1996).

* cited by examiner

*Primary Examiner*—Terry McKelvey
*Assistant Examiner*—William Sandals
(74) *Attorney, Agent, or Firm*—Finnegan, Henderson, Farabow, Garrett & Dunner, L.L.P.

(57) ABSTRACT

The present invention provides a process for producing S-hydroxynitrile lyase, comprising the steps of culturing in a medium yeast cells transformed with recombinant DNA comprising an expression vector into which a S-hydroxynitrile lyase (EC 4.1.2.37) coding gene derived from cassava (*Manihot esculenta*) has been incorporated, and collecting S-hydroxynitrile lyase from the yeast cells. According to the present invention, a large amount of S-hydroxynitrile lyase can be efficiently produced by genetic engineering techniques.

13 Claims, No Drawings

SEQUENCE LISTING

<160> NUMBER OF SEQ ID NOS: 6

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 1
ggggaattca tggtaactgc acattttgtt ctgattc                              37

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ggggtcgacc tcacggatta gaagccgccg                                      30

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 3
gggggatcca ccatggtaac tgcacatttt gttctgattc                           40

<210> SEQ ID NO 4

```
<211> LENGTH: 28
<212> TYPE: DNA
<213> ORGANISM: Artificial Sequence
<220> FEATURE:
<223> OTHER INFORMATION: Description of Artificial  Sequence: Primer

<400> SEQUENCE: 4
gggtacgtat caagcatatg catcagcc                                          28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial  Sequence: Primer

<400> SEQUENCE: 5
ggggaattca tggtaactgc acattttg                                          28

<210> SEQ ID NO 6
<211> LENGTH: 30
<212> TYPE: DNA
<213> ORGANISM: Artificial Sequence
<220> FEATURE:
<223> OTHER INFORMATION: Description of Artificial  Sequence: Primer

<400> SEQUENCE: 6
taggagctgc aggcttcaag catatgcatc                                        30
```

PROCESS FOR PRODUCING S-HYDROXYNITRILE LYASE

BACKGROUND OF THE INVENTION

1. Field of the Invention

The present invention relates to a process for producing S-hydroxynitrile lyase using a recombinant yeast cell into which S-hydroxynitrile lyase coding gene derived from cassava (*Manihot esculenta*) is introduced.

2. Description of the Prior Art

S-hydroxynitrile lyase derived from cassava (EC 4.1.2.37) is an enzyme useful for synthesis of optically active S-cyanohydrins from aromatic and/or aliphatic carbonyl compounds and hydrocyanic acid. Synthesis of optically active cyanohydrins using the enzyme is very useful for synthesis of various optically active intermediates.

However, it has been difficult to industrially utilize the present enzyme since cassava tissue contains an extremely low amount of the enzyme. One example of process for producing the enzyme is conventionally known, which comprises the steps of growing *E. coli* transformed with recombinant DNA into which S-hydroxynitrile lyase coding gene derived from cassava has been introduced. (Angew. Chem. Int. Ed. Engl. 35, 437–439, 1996; Biotechnol. Bioeng. 53, 332–338, 1997). However, such a process using *E. coli* as a host had several disadvantages including: a low productivity of the enzyme; and requirements to add expensive antibiotics and/or an inducer substrate to medium for producing a large amount of the enzyme. Because of these problems, it has been difficult to accomplish a process for efficient production of the enzyme with reduced cost.

OBJECTS AND SUMMARY OF THE INVENTION

The object of the present invention is to provide a process for producing a large amount of S-hydroxynitrile lyase by genetic-engineer technique.

After intensive studies, the present inventors finally succeeded in production of a large amount of S-hydroxynitrile lyase using yeast rather than using *E. coli* as a host for expression of S-hydroxynitrile lyase coding gene derived from cassava.

The present invention generally relates to a process for producing S-hydroxynitrile lyase, comprising the steps of culturing, in a medium, yeast cells transformed with recombinant DNA consisting of an expression vector into which S-hydroxynitrile lyase (EC 4. 1. 2. 37) coding gene derived from cassava (*Manihot esculenta*) has been incorporated, and collecting S-hydroxynitrile lyase from the culture.

Particularly, the present invention relates to the followings:

(1) a process for producing S-hydroxynitrile lyase, comprising the steps of culturing, in a medium, yeast cells transformed with recombinant DNA consisting of yeast episome expression vector into which S-hydroxynitrile lyase (EC 4. 1. 2. 37) coding gene derived from cassava (*Manihot esculenta*) has been incorporated, and collecting S-hydroxynitrile lyase from the culture;

(2) a process for producing S-hydroxynitrile lyase, comprising the steps of culturing, in a medium, the yeast Saccharomyces transformed with recombinant DNA consisting of yeast integrating expression vector into which S-hydroxynitrile lyase (EC 4. 1. 2. 37) coding gene derived from Cassava (*Manihot esculenta*) has been incorporated, and collecting S-hydroxynitrile lyase from the culture; and (3) a process for producing S-hydroxynitrile lyase, comprising the steps of culturing, in a medium, the yeast Pichia transformed with recombinant DNA consisting of yeast integrating expression vector into which S-hydroxynitrile lyase (EC 4.1.2.37) coding gene derived from cassava (*Manihot esculenta*) has been incorporated, and collecting S-hydroxynitrile lyase from the culture.

This specification includes all or part of the contents as disclosed in the specification of Japanese Patent Applications Nos. 373246/1998, 373247/1998 and 373248/1998, which are priority documents of the present application.

DETAILED DESCRIPTION OF THE INVENTION

The present invention will be hereinafter described in detail.

In accordance with the present invention, S-hydroxynitrile lyase coding gene of interest derived from cassava is cloned at first. The DNA sequence of the enzyme is well known and has been already disclosed. (Arch. Biochem, Biophys. 311, 496–502, 1994). Total mRNA including mRNA of the enzyme gene is extracted from cassava leaves and cDNA thereof is synthesized according to any conventional method. The enzyme coding gene is amplified by PCR using primers designed based on the well-known sequence data of S-hydroxynitrile lyase cDNA.

Next, an expression cassette was constructed by inserting a transcription promoter at upstream site and a transcription-terminator at downstream site of the enzyme gene to allow the enzyme gene obtained as described above to express in the recombinant yeast cells, and the constructed expression cassette is then introduced into an expression vector. Alternatively, where transcription promoter and terminator are already present in an expression vector into which the enzyme gene is to be introduced, the transcription promoter and terminator may be used and only the enzyme gene may be introduced therebetween, i.e., there is no need to construct an expression cassette. In either cases, multiple expression cassettes can be present in one expression vector.

Since the expression level of the enzyme greatly depends on the selection of a promoter to be used in an expression cassette, appropriate promoter should be selected. Examples of yeast promoter for efficient expression of the introduced gene in a yeast cell include native promoters such as PGK, GAP, TPI, GAL1, GAL10, ADH2, PHO5, CUP1 and MFα1, recombinant promoters such as PGK/α2 operator, GAP/GAL, PGK/GAL, GAP/ADH2, CYC/GRE and PGK/ARE, and mutated promoters such as Leu2-d. Particularly, GAP promoter is preferred.

Each of the promoters described above may have DNA consisting of the nucleotide sequence of a native promoter, or DNA consisting of the native promoter sequence having deletion, substitution and/or addition of one or more bases but still retaining the promoter activity. Deletion, substitution or addition of base(s) may be generated by using any conventional techniques such as site-directed mutagenesis.

On the other hand, transcription-terminator may be present downstream of the enzyme gene to allow efficient transcription-termination to obtain maximum gene expression. Examples of such transcription-terminator include ADH1, TDH1, TFF and TRP5.

Where the yeast Pichia is used as a host to be transformed, promoter in such an expression cassette as described above may be one which promotes enzyme expression within a methanol-utilizing strain in the yeast Pichia in the presence of methanol carbon source. Terminator in such an expression cassette may be one which allows efficient transcription-termination to obtain maximum gene expression. Particularly, AOX1 promoter and AOX1 terminator are preferred.

According to one embodiment of the present invention, yeast episome expression vector (autonomously replicating plasmid) is used as expression vector.

Yeast episome plasmid vector contains $2\mu$ plasmid sequence, which is native to yeast. The vector can be replicated within a host yeast cell by utilizing the replication origin of the $2\mu$ plasmid sequence.

Yeast episome expression vector to be used in the present invention may not be limited to particular vectors as long as it comprises at least ORI sequence of yeast $2\mu$ plasmid sequence and can be autonomously replicated in a host yeast cell. Examples of such vector include YEp51, pYES2, YEp351 and YEp352 but are not limited thereto.

Preferably, the above-described yeast episome expression vector may be a shuttle vector which can replicate in a $E.$ $coli$ cell for subcloning in the recombinant $E.$ $coli.$ More preferably, such expression vectors may also contain a selective marker gene such as ampicillin-resistant gene. Also, such expression vectors contain a marker gene by which yeast clones can be selected depending on their auxotrophy and/or drug-resistance when recombinant yeast is prepared. Examples of marker gene include HIS3, TRP1, LEU2, URA3, LYS2, Tn903 kan$^r$, Com$^r$, Hyg$^r$, CUP1 and DHFR though they are not limited thereto. Preferably, a marker gene should be selected based on the genomic-type of the host Saccharomyces to be used for gene introduction.

Particular examples of the above-described yeast episome expression vector to be used in the present invention include: a vector constructed by incorporating GAP promoter into the multi-cloning site of yeast expression vector YEp352, S-hydroxynitrile lyase coding gene into downstream of the promoter and a terminator into further downstream (designated as YEp352-GC); a vector constructed by incorporating S-hydroxynitrile lyase coding gene into the multi-cloning site downstream of GAL 10 promoter in yeast expression vector YEp51 (designated as YEp51-C); a vector constructed by incorporating GAP promoter into the multi-cloning site of yeast expression vector YE351, S-hydroxynitrile lyase coding gene into downstream of the promoter and a terminator into further downstream (designated as YEp351-GC); and a vector constructed by incorporating S-hydroxynitrile lyase coding gene into the multi-cloning site downstream of GAL 1 promoter in yeast expression vector pYES2 (designated as pYES2-C).

According to another embodiment of the present invention yeast integrating expression vector (which can be integrated into chromosomal DNA) is used as expression vector.

Although yeast integrating plasmid vector has a DNA sequence (normally a selective marker gene sequence) homologous to that of yeast chromosome, it cannot be replicated as a plasmid in a yeast cell. Such yeast integrating plasmid vector can remain in yeast cells only when homologous replacement occurs between the sequence on the vector homologous to yeast chromosome and the yeast chromosome gene thereby integrating the plasmid vector into the chromosome. The integrated gene is known to be stably retained within the yeast cell even not under growth conditions where expression of selected marker gene is essential.

Yeast integrating expression vector to be used in the present invention is not limited to particular ones as long as it allows integration of S-hydroxynitrile lyase coding gene derived from cassava carried by the vector into yeast chromosome. For example, when incorporated into chromosome of Saccharomyces, yeast integrating vectors such as pRS303 and pRS304, or modified vectors constructed by excising yeast $2\mu$ plasmid-derived sequence from vectors derived from yeast $2\mu$ such as YEp51, pYES2, YEp351 and YEp352 and then cyclizing the vectors may be preferably used. Vectors for integration into the chromosome of a methanol-utilizing strain in the yeast Pichia are not limited to but include pPIC3.5K, pPIC9K and pAO815.

Yeast integrating expression vectors described above may be preferably shuttle vectors which can replicate in $E.$ $coli$ cells for subcloning in the recombinant $E.$ $coli$ cells. More preferably, such yeast expression vectors contain selective marker genes such as ampicillin-resistant genes. Alternatively, such expression vectors contain marker genes by which yeast clones can be selected depending on auxotrophy and drug resistance when recombinant yeast is prepared. Examples of marker gene for introduction into the yeast Saccharomyces include HIS3, TRP1, LEU2, URA3, LYS2, Tn903 kan$^r$, Cm$^r$, Hyg$^r$, CUP1 and DHFR though they are not limited thereto. A marker gene should be selected depending on the genomic-type of the host Saccharomyces strain into which the gene is to be introduced. Examples of marker gene for introduction into the yeast Pichia include HIS4 and kan$^r$ though they are not limited thereto. A marker gene should be selected depending on the genomic-type of the host Pichia strain into which the gene is to be introduced.

According to one embodiment of the present invention, the yeast Saccharomyces is used as a host though the host to be used in the present invention is not limited thereto as long as it can stably retain such an expression cassette after introduction of the cassette. Example of the yeast Saccharomyces include *Saccharomyces cerevisiae* KK4, Y334, Inv-Sc1 and W303 strains. Further, both haploid and diploid strains of these host yeast may be used.

According to another embodiment of the present invention, although a methanol-utilizing strain in the yeast Pichia is used as a host, yeast is not limited to particular ones as long as it can retain such an expression cassette after introduction of the cassette. Examples of methanol-utilizing strains in the yeast Pichia include *Pichia pastoris* KM71 and GS115 strains. Both haploid and diploid of these host yeast may be used.

In accordance with conventional transformation technique, recombinant yeast having an ability to produce S-hydroxynitrile lyase of interest can be obtained by introducing, into any of the above-described hosts, a yeast episome expression vector into which S-hydroxynitrile lyase coding gene derived from cassava is incorporated.

S-hydroxynitrile lyase can be produced by culturing the obtained recombinant yeast in a medium.

Medium may be conveniently supplemented with nitrogen sources such as yeast nitrogen base w/o amino acids (Difco Laboratories), essential amino acids and casamino acid, carbon sources such as glucose, galactose, raffinose and other saccharides, or alcohol such as glycerol and ethanol. The medium may be appropriately adjusted to pH 4–7.

According to the present invention, for culturing yeast transformed with yeast episome expression vector, composition of medium may be preferably altered depending on the selective marker gene on the vector to be used in order to prevent deletion of the enzyme gene present in the recombinant yeast cells. For example, medium which does not substantially contain uracil is selected for recombinant yeast transformed with yeast episome expression vector YEp352-GC where the selection marker gene is URA3. Alternatively, medium which does not substantially contain L-leucine is selected for recombinant yeast transformed with yeast episome expression vector YEp351-GC where the selective marker gene is LEU2.

Preferably, an inducer substrate may be added to the medium depending on the promoter to be used where enzyme production is required to be induced. For example, where promoter expression is promoted or inhibited by a particular carbon source, an appropriate carbon source should be selected for each case.

Where the expression of the enzyme gene is controlled by GAP promoter, which is one of the promoters preferable for the present invention, any carbon source which can be utilized by the host yeast cells may be used since the promoter will constitutively express.

On the other hand, for culturing yeast transformed with yeast integrating expression vector, medium may be suitably selected for growth of the host yeast to be used. There is no limitation to nutritional source nor need to add any antibiotics since the enzyme gene may be stably retained in the recombinant yeast cells. Preferably, medium may be adjusted to pH4–7.

Preferably, an inducer substrate may be added to the medium depending on the promoter to be used where enzyme production is required to be induced. For example, where promoter expression is promoted or inhibited by a particular carbon source, an appropriate carbon source should be selected for each case.

Where the expression of the enzyme gene is controlled by GAP promoter, which is one of the promoters suitable for the present invention, any carbon source which can be utilized by the host yeast cells may be used since the promoter will constitutively express.

On the other hand, where expression of the enzyme gene is controlled by AOX1 promoter, which is one of promoters suitable for the present invention, preferably glucose may not be added since it may repress/inhibit the expression though glycerol and raffinose do not affect the enzyme gene expression. Moreover, methanol may be preferably added to the culture for efficient expression of the enzyme gene and thus for production of a large amount of the enzyme since it will promote the gene expression.

The cells are cultured at 25–35° C. for several hours to three days, for example, until the growth reaches at its stationary phase.

The recombinant yeast cells cultured as described above can produce a large amount of S-hydroxynitrile lyase.

Subsequently, S-hydroxynitrile lyase may be collected from the culture by using conventional enzyme collection methods including: cell lysis using cell-wall digesting enzyme (zymolyase); ultrasonication; disruption using glass beads; extraction with surfactants; self-digestion; and freezing-thawing method. Next, undissolved materials may be removed by, for example, filtration or centrifugation to give crude enzyme solution containing S-hydroxynitrile lyase.

S-hydroxynitrile lyase may be further purified from the crude enzyme solution by using any conventional protein purification method alone or in combination, including: ammonium sulfate fractionation; organic solvent precipitation; adsorption with ion exchanger; ion exchange chromatography; hydrophobic chromatography; gel filtration chromatography; affinity chromatography; and electrophoresis.

Effect of the Invention

According to the present invention, an efficient process for producing a large amount of S-hydroxynitrile lyase is provided using genetic-engineering technique.

PREFERRED EMBODIMENTS OF THE INVENTION

Hereinafter the present invention will be described in detail by way of unlimiting examples.

EXAMPLE I

Preparation of cDNA from Cassava Tissue and Sassava Derived S-hydroxynitrile Lyase Gene Total mRNA was extracted from cassava leaves. The extracted mRNA was used as template to synthesize cDNA. Thus, cDNA library was prepared from cassava. The following PCR primers were synthesized based on the sequence data of S-hydroxynitrile lyase coding gene derived from cassava (see Arch. Biochem. Biophys. 311, 496–502, 1994).

Sense primer: GGG GAA TTC ATG GTA ACT GCA CAT TTT GTT CTG ATT C (SEQ ID NO: 1)

Anti-sense primer: GGG GTC GAC CTC ACG GAT TAG AAG CCG CCG (SEQ ID NO: 2)

Performing PCR of the cDNA prepared as described above using these primers (at 95° C. for 0.5 min, at 55° C. for 0.5 min and at 72° C. for 1 min: 35 cycles in total) gave a gene corresponding to S-hydroxynitrile lyase coding gene. Analysis of the DNA sequence showed that it was the same as that disclosed in the publication (supra).

EXAMPLE II

Expression of the Enzyme Gene in Recombinant Yeast Cells (1)

YEp352-GAP vector consisting of YEp352 plasmid vector into which GAP promoter and terminator were incorporated into its multi-cloning site was used to construct yeast episome expression vector YEp352-GC by inserting the cDNA of S-hydroxynitrile lyase obtained in Example I above between the GAP promoter and terminator of the YEp352-GAP vector. The YEp352-GC was *E. coli*-yeast shuttle vector which contained ampicillin-resistant gene, a sequence derived from yeast 2μ plasmid and URA3 sequence which is the selective marker gene for the recombinant yeast.

The expression vector YEp352-GC was used to transform the host yeast *Saccharomyces cerevisiae* Inv-Sc1 strain. Recombinant clone was selected in minimal selection medium without uracil having the following composition:

TABLE 1

| Yeast nitrogen base without amino acids (Difco Laboratories) | 6.7 g/L |
|---|---|
| glucose | 20 g/L |
| adenine | 40 mg/ml |
| L - arginine | 20 mg/ml |
| L - aspartic acid | 100 mg/ml |
| L - glutamic acid | 100 mg/ml |
| L - histidine | 20 mg/ml |
| L - isoleucine | 30 mg/ml |
| L - lysine | 30 mg/ml |
| L - methionine | 20 mg/ml |
| L - phenylalanine | 50 mg/ml |
| L - serine | 375 mg/ml |

TABLE 1-continued

| | |
|---|---|
| L - threonine | 200 mg/ml |
| L - tryptophan | 40 mg/ml |
| L - tyrosine | 30 mg/ml |
| L - valine | 150 mg/ml |
| L - leucine | 60 mg/ml |

The recombinant yeast cells (YEp352-GC-S2) obtained as described above were cultured in YNBDCas liquid medium having the following composition for 24 hours and the enzyme activity was determined as will be described.

TABLE 2

| | |
|---|---|
| Yeast nitrogen base without amino acids (Difco Laboratories) | 6.7 g/L |
| glucose | 20 g/L |
| casamino acid | 20 g/L |
| L - tryptophan | 40 mg/ml |

First, 1 ml of the culture solution containing the recombinant cells was centrifuged to collect the cells. Next, 0.1 ml of 0.5 mm glass beads was added to the collected cells which were then frozen with liquid nitrogen. Subsequently, after 0.2 ml of 0.15M sodium citrate buffer (pH5) was added, the cells were disrupted by stirring. Solution containing the disrupted cells was centrifuged to remove the supernatant which was used for enzyme activity assay. Change in absorbance of the supernatant was monitored at 249.6 nm while the enzyme decomposed a substrate (DL-mendelonitorile) to produce benzaldehyde. Then, the enzyme activity was calculated from the determined absorbance and expressed in units (one unit corresponds to the activity of the enzyme to decompose 1$\mu$ mol of substrate per minute).

S-hydroxynitrile lyase activity per ml of culture solution containing the recombinant cells (YEp352-GC-S2 strain) was determined to be 1.126 unit/ml (specific activity: 1.33 unit/mg protein).

EXAMPLE III

Enzyme Gene Expression in Recombinant Yeast Cells (2)

An expression cassette was isolated with restriction enzyme BamHI from the plasmid YEp352-GC prepared as described in Example II. On the other hand, the sequence derived from yeast 2$\mu$ plasmid in YEp351 was excised therefrom with AatII and HpaI, and then the cleaved product was recyclized to give YIp351. Then the YIp351 was cleaved with BamHI at its cloning site. The BamHI-cleaved YIp351 was ligated to the above-described expression cassette to give plasmid YIp351-2XGC (yeast integrating expression vector) sequentially comprising two expression cassettes in tandem.

This plasmid was cleaved with BstXI at its Leu 2 sequence to give a linear recombinant DNA which was used to transform host yeast *Saccharomyces cerevisiae* Inv-Sc1 strain to give transformant. This transformant (YIp351-2XGC-70-55 strain) was grown in YPD medium (1% yeast extract, 2% peptone and 2% glucose) and similarly determined for the enzyme activity as described in Example II.

S-hydroxynitrile lyase activity per ml of the culture solution containing the recombinant cells (YIp351-2XGC-70-55 strain) was determined to be 2.15 unit/ml (specific activity: 1.09 unit/mg protein).

EXAMPLE IV

Enzyme Gene Expression in Recombinant Yeast Cells (3)

YIp351-2XGC prepared in Example III was digested with restriction enzymes SacI and SalI to excise its expression cassette region which was then incorporated into pRS303 at the cloning site to construct yeast integrating expression vector pRS303-2XGC. This vector plasmid was cleaved with a restriction enzyme at approximately the middle of its HIS3 sequence to give a linear DNA which was then used to transform the host cells, the recombinant yeast cells obtained in Example III (YIp351-2XGC-70-55). Selected transformant (YIp351-2XGC-S1 strain) was grown in YPD medium as described above and similarly determined for S-hydroxynitrile lyase activity per ml of the solution to be 3.157 unit/ml solution (specific activity: 1.24 unit/mg protein).

EXAMPLE V

Enzyme Gene Expression in Recombinant Yeast Cells (4)

As describe in Example IV, an expression cassette region in which two expression cassettes were inserted in tandem was excised from YIp351-2XGC prepared in Example III with restriction enzymes SacI and PstI, and was integrated into the cloning site of pRS304 to construct a yeast integrating vector pRS304-2XGC. This vector plasmid was cleaved with a restriction enzyme at approximately the middle of its TRP1 sequence to give a linear DNA which was then used to transform the host cells, the recombinant yeast cells obtained in Example 4 (YIp351-2XGC-S1). Selected transformant (pRS304-2XGC-33strain) was grown in YPD medium as described above and similarly determined for S-hydoxynitrile lyase activity per ml of the solution to be 1.51 unit/mg protein (specific activity).

EXAMPLE VI

Enzyme Gene Expression in Recombinant Yeast Cells (5)

As described in Example V, an expression cassette region in which two expression cassettes were inserted in tandem was excised from YIp351-2XGC prepared in Example III with restriction enzymes XbaI and Sal. On the other hand, the sequence derived from yeast 2$\mu$ plasmid in YEp352 was excised therefrom and then the cleaved product was recyclized to give YIp352. The expression cassette region as prepared above was inserted into the YIp352 to construct plasmid YIp352-2XGC (yeast integrating plasmid) in which two expression cassettes were inserted.

This vector plasmid was cleaved with a restriction enzyme at approximately the middle of its URA3 sequence to give a linear DNA which was then used to transform the host cells, the recombinant yeast cells obtained in Example 5 (pRS304-2XGC-33).

Selected transformant (YIp352-2XGC-194 strain) was grown in YPD medium as described above and similarly determined for S-hydroxynitrile lyase activity per ml of the solution to be 3.47 unit/mg protein (specific activity).

EXAMPLE VII

Enzyme Gene Expression in Recombinant Yeast Cells (6)

As described in Example I, the following PCR primers were synthesized based on the sequence data of S-hydroxynitrile lyase coding gene derived from cassava.

Sense primer: GGG GGA TCC ACC ATG GTA ACT GCA CAT TTT GTT CTG ATT C (SEQ ID NO: 3)
Anti-sense primer: GGG TAC GTA TCA AGC ATA TGC ATC AGC C (SEQ ID NO: 4)

Performing PCR of the cDNA of S-hydroxynitrile lyase prepared as described in Example I using these primers (at 95° C. for 0.5 min, at 55° C. for 0.5 min and at 72° C. for 1 min: 35 cycles in total) gave a gene corresponding to S-hydroxynitrile lyase coding gene. Analysis of the DNA sequence showed that it was the same as that disclosed in the publication (supra).

The cDNA of S-hydroxynitrile lyase obtained in Example 1 was inserted in the multi-cloning site of expression vector for Pichia (pPIC3.5K, Invitrogen) to construct pPIC3.5K-cas plasmid (yeast integrating expression vector). This plasmid was cleaved with a restriction enzyme at approximately the middle portion of its His4 sequence to give a linear recombinant DNA which was then used to transform host yeast *Pichia pastoris* KM71 and GS115 cells, respectively. Selection of the obtained transformants was performed depending on their antibiotic G418-resistance to obtain clones having higher resistance.

The transformants obtained as described above were grown in BMMY medium (1% yeast extract, 2% peptone, 10% 1M phosphate buffer (pH6.0), 1.34% Yeast Nitrogen Base, $4 \times 10^{-5}$% biotin, 1% methanol) and similarly determined for the enzyme activity.

S-hydroxynitrile lyase activity per ml of culture solutions was determined for the recombinant cells derived from KM-71 strain to be 6.25 unit/ml (specific activity: 2.77 unit/mg protein), and for those from GS-115 strain to be 4.96 unit/ml (specific activity: 1.23 unit/mg protein).

Comparative Example I

Enzyme Gene Expression in Recombinant *E. coli* Cells

Procedure of Example I was repeated except for using the following primers to obtain a gene corresponding to S-hydroxynitrile lyase coding gene.
Sense Primer: GGG GAA TTC ATG GTA ACT GCA CAT TTT G (SEQ ID NO: 5)
Antisense Primer: TAG GAG CTG CAG GCT TCA AGC ATA TGC ATC (SEQ ID NO: 6)

The-above described gene was inserted between BamHI and PstI sites in the multi-cloning site of a vector for *E. coli* (pKK223-3, Pharmacia Biotech) to give a recombinant vector. This vector plasmid was introduced into *E. coli* to obtain recombinant *E. coli* cells. The recombinant *E. coli* cells were cultured in LB medium containing 1 mM IPTG as inducer substrate and ampicillin 0.1 g/L as antibiotics. The culture solution was determined for the enzyme activity to be 0.964 unit/ml (specific activity: 0.545 unit/mg protein).

All publications, including patent and patent applications cited herein are incorporated herein by reference in their entirety.

What is claimed is:

1. A process for producing S-hydroxynitrile lyase, comprising the steps of: culturing in a medium yeast cells transformed with recombinant DNA comprising an expression vector into which S-hydroxynitrile lyase (EC 4.1.2.37) coding gene from cassava (*Manihot esculenta*) has been incorporated, and collecting S-hydroxynitrile lyase from the yeast cells.

2. A process for producing S-hydroxynitrile lyase, comprising the steps of culturing in a medium a yeast cell transformed with recombinant DNA comprising a yeast episome expression vector into which S-hydroxynitrile lyase (EC4.1.2.37) coding gene from cassava (*Manihot esculenta*) is incorporated, and collecting S-hydroxynitrile lyase from the yeast cells.

3. The process of claim 2 wherein said yeast episome expression vector contains DNA comprising the nucleotide sequence of a GAP (glycerol aldehyde phosphate dehydrogenase) promoter from the yeast Saccharomyces, or DNA comprising the GAP promoter sequence having deletion, substitution or addition of one or more bases while still functioning as a promoter.

4. A process for producing S-hydroxynitrile lyase in yeast, comprising the steps of: culturing in a medium the yeast Saccharomyces transformed with recombinant DNA comprising a yeast integrating expression vector into which S-hydroxynitrile lyase (EC 4.1.2,37) coding gene from cassava (*Manihot esculenta*) is incorporated, and collecting S-hydroxynitrile lyase from the yeast cells.

5. The process of claim 4 wherein said yeast integrating expression vector contains DNA comprising the nucleotide sequence of a GAP (glycerol aldehyde phosphate dehydrogenase) promoter from the yeast Saccharomyces, or DNA comprising the GAP promoter sequence having deletion, substitution or addition of one or more bases while still functioning as a promoter.

6. A process for producing S-hydroxynitrile lyase in yeast, comprising the steps of: culturing in a medium the yeast Pichia transformed with recombinant DNA comprising a yeast integrating expression vector into which S-hydroxynitrile lyase (EC 4.1.2.37) coding gene from cassava (*Manihot esculenta*) is incorporated, and collecting S-hydroxynitrile lyase from the yeast cells.

7. The process of claim 6 wherein said yeast integrating expression vector contains DNA comprising the nucleotide sequence of an AOXI (alcohol oxidase) promoter derived from the yeast Pichia, or DNA consisting of the AOX1 promoter sequence having deletion, substitution or addition of one or more bases while still functioning as a promoter.

8. The process of claim 1 wherein the yeast cells are those of a diploid strain.

9. The process of claim 1 wherein the yeast cells are those of a haploid strain.

10. The process of claim 4 wherein the Saccharomyces yeast cells are of a diploid strain.

11. The process of claim 10 wherein the diploid Saccharomyces yeast cells are of the strain KK4, Y334, Inv-Sc1, or W303.

12. The process of claim 4 wherein the Saccharomyces yeast cells are of a haploid strain.

13. The process of claim 12 wherein the haploid Saccharomyces yeast cells are of the strain KK4, Y334, Inv-Sc1, or W303.

* * * * *